(12) United States Patent
Ogawa

(10) Patent No.: US 9,186,796 B2
(45) Date of Patent: Nov. 17, 2015

(54) MASTER INPUT DEVICE AND MASTER-SLAVE MANIPULATOR

(75) Inventor: Ryohei Ogawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/403,102

(22) Filed: Feb. 23, 2012

(65) Prior Publication Data

US 2012/0221145 A1    Aug. 30, 2012

(30) Foreign Application Priority Data

Feb. 24, 2011    (JP) .................................. 2011-038796

(51) Int. Cl.
| | |
|---|---|
| G05B 15/00 | (2006.01) |
| G05B 19/00 | (2006.01) |
| B25J 13/02 | (2006.01) |
| B25J 3/04 | (2006.01) |
| A61B 19/00 | (2006.01) |

(52) U.S. Cl.
CPC .............. *B25J 13/02* (2013.01); *A61B 19/2203* (2013.01); *B25J 3/04* (2013.01); *A61B 19/56* (2013.01); *A61B 2019/2223* (2013.01); *A61B 2019/2269* (2013.01); *A61B 2019/5255* (2013.01)

(58) Field of Classification Search
CPC .................. A61B 19/22; A61B 19/56; A61B 2019/2223; A61B 2019/2269; A61B 2019/5255; A61B 19/2203; A61B 19/5212; B25J 3/04; B25J 13/02; B25J 13/04
USPC ................. 700/254, 257, 258, 253, 245, 262; 600/102, 103, 118, 130; 414/4, 5, 7; 318/568, 632
See application file for complete search history.

(56) References Cited

U.S. PATENT DOCUMENTS

| | | | |
|---|---|---|---|
| 5,279,309 A | | 1/1994 | Taylor et al. |
| 5,874,540 A | * | 2/1999 | Hansen et al. ............. 530/387.3 |
| 5,876,325 A | * | 3/1999 | Mizuno et al. ................ 600/102 |
| 6,120,433 A | * | 9/2000 | Mizuno et al. ................ 600/102 |

(Continued)

FOREIGN PATENT DOCUMENTS

| | | |
|---|---|---|
| DE | 10 2010 023 736 A1 | 1/2011 |
| JP | 62-212710 A | 9/1987 |

(Continued)

OTHER PUBLICATIONS

JP2001-145639A_English_machine_translation.*

(Continued)

*Primary Examiner* — Jason Holloway
*Assistant Examiner* — Rachid Bendidi
(74) *Attorney, Agent, or Firm* — Scully, Scott, Murphy & Presser, P.C.

(57) ABSTRACT

A master input device operates a slave manipulator which includes joints corresponding to a plurality of degrees of freedom. The device includes an operating unit and detection units of two or more systems. The operating unit is capable of being changed in position and orientation by an operator's operation. The operating unit is provided command values of a position and orientation of the slave manipulator as the position and orientation thereof change. The detection units individually detect different physical quantities related to the operating unit in order to detect the position and orientation of the operating unit.

5 Claims, 10 Drawing Sheets

(56) References Cited

U.S. PATENT DOCUMENTS

| | | | |
|---|---|---|---|
| 6,496,756 B1* | 12/2002 | Nishizawa et al. | 700/264 |
| 6,574,355 B2* | 6/2003 | Green | 382/128 |
| 6,699,177 B1* | 3/2004 | Wang et al. | 600/102 |
| 8,009,140 B2* | 8/2011 | Kishi et al. | 345/156 |
| 2004/0034302 A1 | 2/2004 | Abovitz et al. | |
| 2005/0107916 A1* | 5/2005 | Nagasaka | 700/245 |
| 2006/0204232 A1 | 9/2006 | Weinberg et al. | |
| 2008/0161830 A1* | 7/2008 | Sutherland et al. | 606/130 |
| 2008/0180392 A1* | 7/2008 | Kishi et al. | 345/156 |
| 2008/0215065 A1* | 9/2008 | Wang et al. | 606/130 |
| 2008/0234866 A1* | 9/2008 | Kishi et al. | 700/259 |
| 2008/0245175 A1* | 10/2008 | Jinno et al. | 74/490.01 |
| 2009/0154910 A1* | 6/2009 | Weinberg et al. | 396/50 |
| 2009/0192523 A1* | 7/2009 | Larkin et al. | 606/130 |
| 2010/0332031 A1* | 12/2010 | Itkowitz et al. | 700/245 |
| 2011/0160745 A1* | 6/2011 | Fielding et al. | 606/130 |
| 2011/0282493 A1* | 11/2011 | Ortmaier | 700/261 |

FOREIGN PATENT DOCUMENTS

| | | | |
|---|---|---|---|
| JP | 6-168530 | | 6/1994 |
| JP | 7-68480 A | | 3/1995 |
| JP | 07-276265 | | 10/1995 |
| JP | 08-280697 | | 10/1996 |
| JP | 09-216183 | | 8/1997 |
| JP | 2000-025389 | | 1/2000 |
| JP | 2001-087281 | | 4/2001 |
| JP | 2001-145639 A | * | 5/2001 |
| JP | 2003-265500 A | | 9/2003 |
| JP | 2004-50356 A | | 2/2004 |
| JP | 2007-11978 A | | 1/2007 |
| JP | 2007011978 A | * | 1/2007 |
| JP | 2009-184035 A | | 8/2009 |
| JP | 2010-273765 | | 12/2010 |
| JP | 2010-284781 A | * | 12/2010 |
| TW | 200644620 A | | 12/2006 |

OTHER PUBLICATIONS

JP2010-284781A_English_machine_translation.*
EnglishTranslation for Reference_ JP 2007-011978.*
JP2001-145639 A_English_machine_translation (May 2001).*
JP2010-284781 A_English_machine_translation (Dec. 2010).*
English translation of International Search Report PCT/JP2012/054315 dated May 1, 2012.
Extended Supplementary European Search Report dated Feb. 5, 2014 in corresponding European Patent Application No. 12749271.8.
European Patent Convention Communication dated Jan. 8, 2015, received in European Application No. 12 749 271.8.
Chinese Office Action dated Nov. 3, 2014 from related Chinese Application No. 201280010006.6, together with an English language translation.
Chinese Office Action dated May 15, 2015 from Chinese Application No. 201280010006.6, together with an English language translation.
Japanese Office Action dated Aug. 18, 2015 from related Japanese Patent Application No. 2011-038796, together with an English language translation.

* cited by examiner

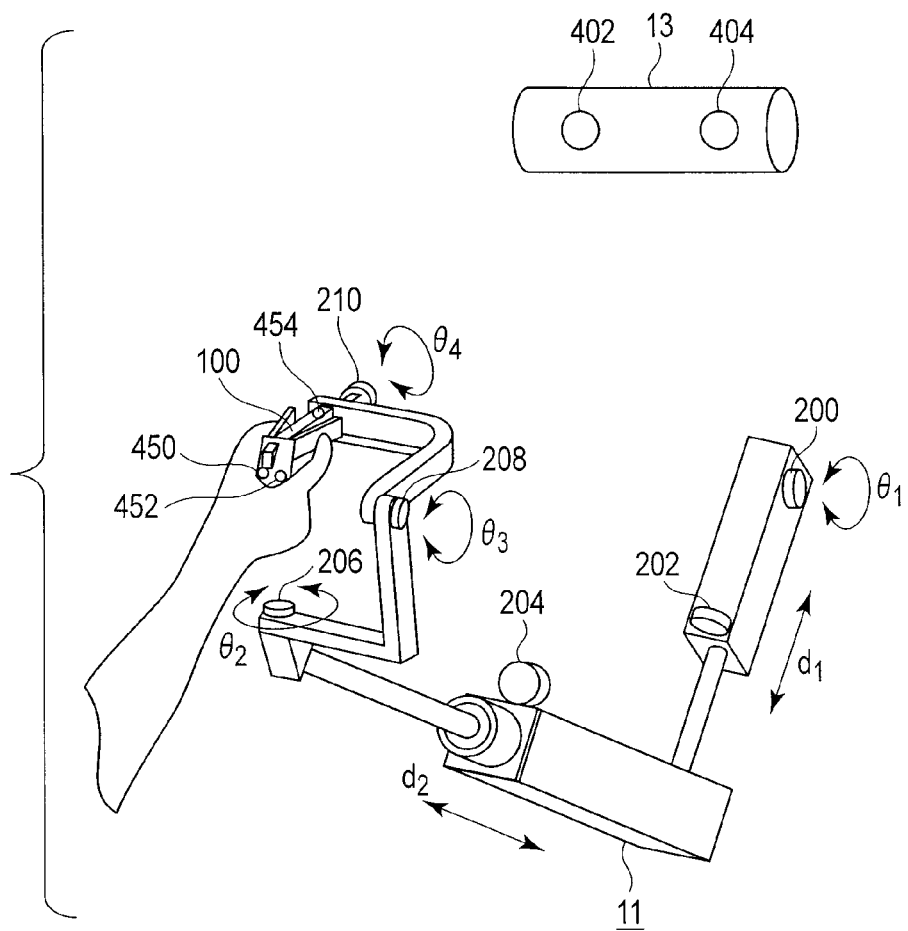
F I G. 2

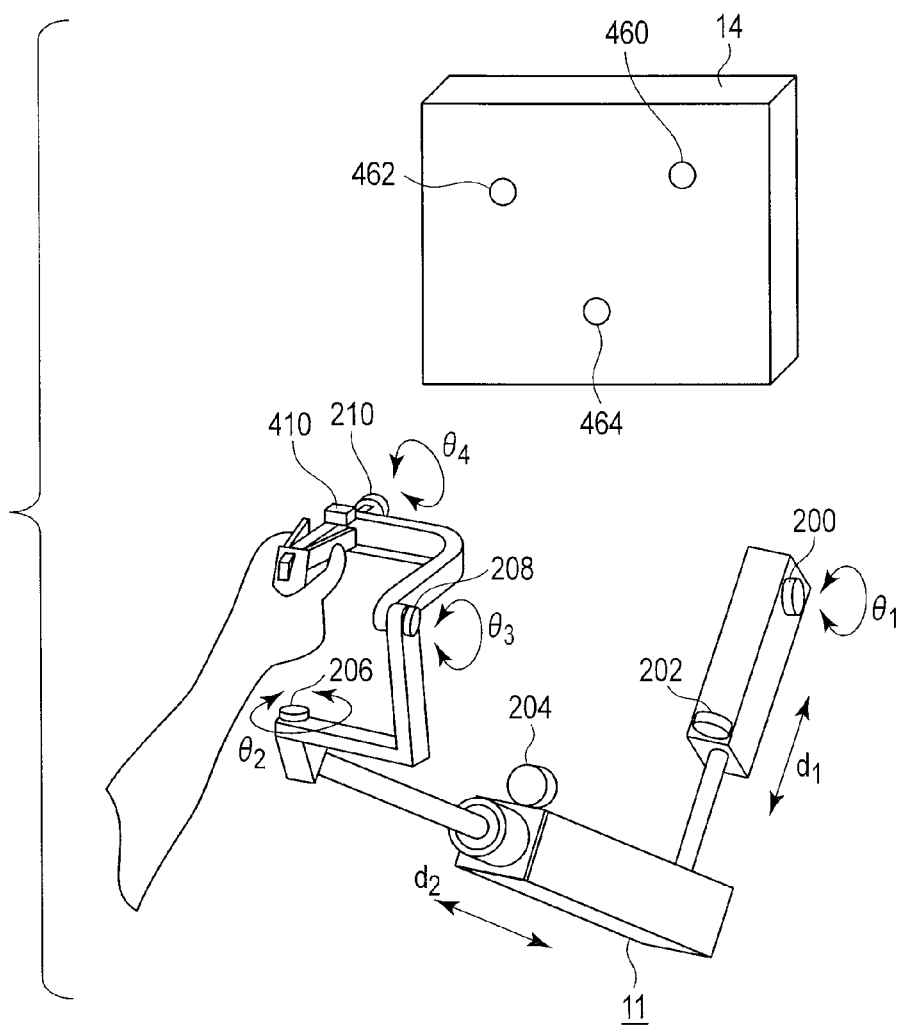
F I G. 4

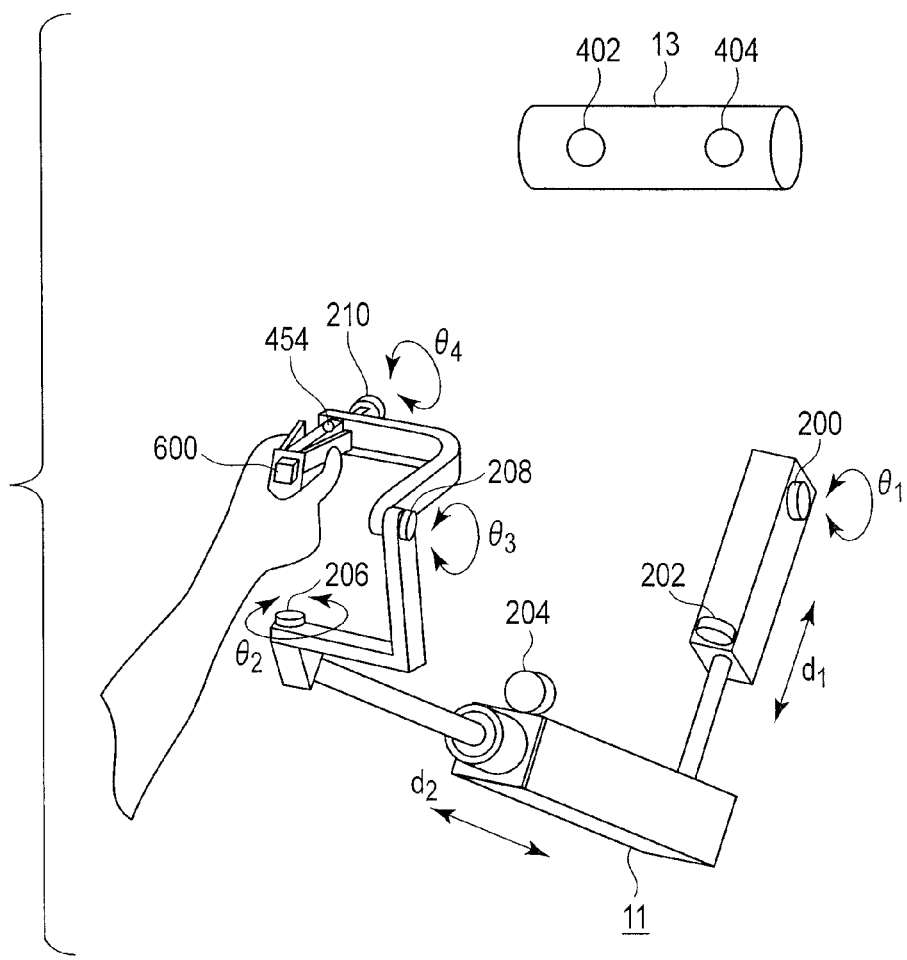
F I G. 5

MASTER INPUT DEVICE AND MASTER-SLAVE MANIPULATOR

CROSS-REFERENCE TO RELATED APPLICATIONS

This application is based upon and claims the benefit of priority from prior Japanese Patent Application No. 2011-038796, filed Feb. 24, 2011, the entire contents of which are incorporated herein by reference.

BACKGROUND OF THE INVENTION

1. Field of the Invention

The present invention relates to a master input device for remotely operating a slave manipulator and a master-slave manipulator comprising the master input device.

2. Description of the Related Art

Robotic surgical treatment has recently been investigated to implement labor-saving medical facilities. In the field of surgery, various proposals are made for manipulator systems in which a manipulator with a multidegree-of freedom (or multi-joint) arm is used for the treatment of a patient. In one such known manipulator system (master-slave manipulator), the manipulator (slave manipulator) configured to directly contacts the patient's body cavity can be remotely operated by a master input device that is located at a distance from the slave manipulator. Normally, in the master-slave manipulator, the position/orientation of an operating unit of the master input device is input as a command value to a controller. In the controller, an inverse kinematics computation for the distal end portion of the slave manipulator is performed based on the command value of the position/orientation of the operating unit. Thereupon, drive amounts of joints of the slave manipulator are calculated, and the joints are drivingly controlled based on the calculated drive amounts. For this control, it is necessary to detect the position/orientation of the operating unit of the master input device. Conventionally, the position/orientation of the master operation input device is detected by means of a sensor attached to the operating unit of the input device.

If the sensor used to detect the position/orientation of the operating unit is of only a single system, the detection cannot be achieved in case of failure of the sensor. A method of duplexing sensors (e.g., Jpn. Pat. Appln. KOKAI Publication No. 6-168530) is a known way to avoid this. If the technique of this patent document is applied to the master input device, the position/orientation of the operating unit of the input device can be detected by means of a sensor of an alternative system in case of failure of a sensor of one system.

BRIEF SUMMARY OF THE INVENTION

According to a first aspect of the invention, there is provided a master input device configured to operate a slave manipulator which comprises joints corresponding to a plurality of degrees of freedom, comprising: an operating unit capable of being changed in position and orientation by an operator's operation and configured to provide command values of a position and orientation of the slave manipulator as the position and orientation thereof change; and detection units of two or more systems configured to individually detect different physical quantities related to the operating unit in order to detect the position and orientation of the operating unit.

According to a second aspect of the invention, there is provided a master-slave manipulator comprising: the master input device of the first aspect; a first control unit configured to calculate a plurality of positions and orientations of the operating unit based on the physical quantities individually detected by the detection units of two or more systems; and a second control unit configured to calculate the command values of the position and orientation of the slave manipulator based on the positions and orientations of the operating unit calculated by the first control unit and drivingly control the slave manipulator based on the calculated command values of the position and orientation of the slave manipulator.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a view illustrating duplexing of sensors for detecting the position/orientation of an operating unit of a master input device according to the first embodiment;

FIG. 4 is a view showing a modification of the first embodiment in which the relative positions of an image sensor and markers are reversed;

FIG. 5 is a view illustrating duplexing of sensors for detecting the position/orientation of an operating unit of a master input device according to a second embodiment of the invention;

DETAILED DESCRIPTION OF THE INVENTION

Embodiments of the present invention will now be described with reference to the accompanying drawings.

First Embodiment

Figure 1:
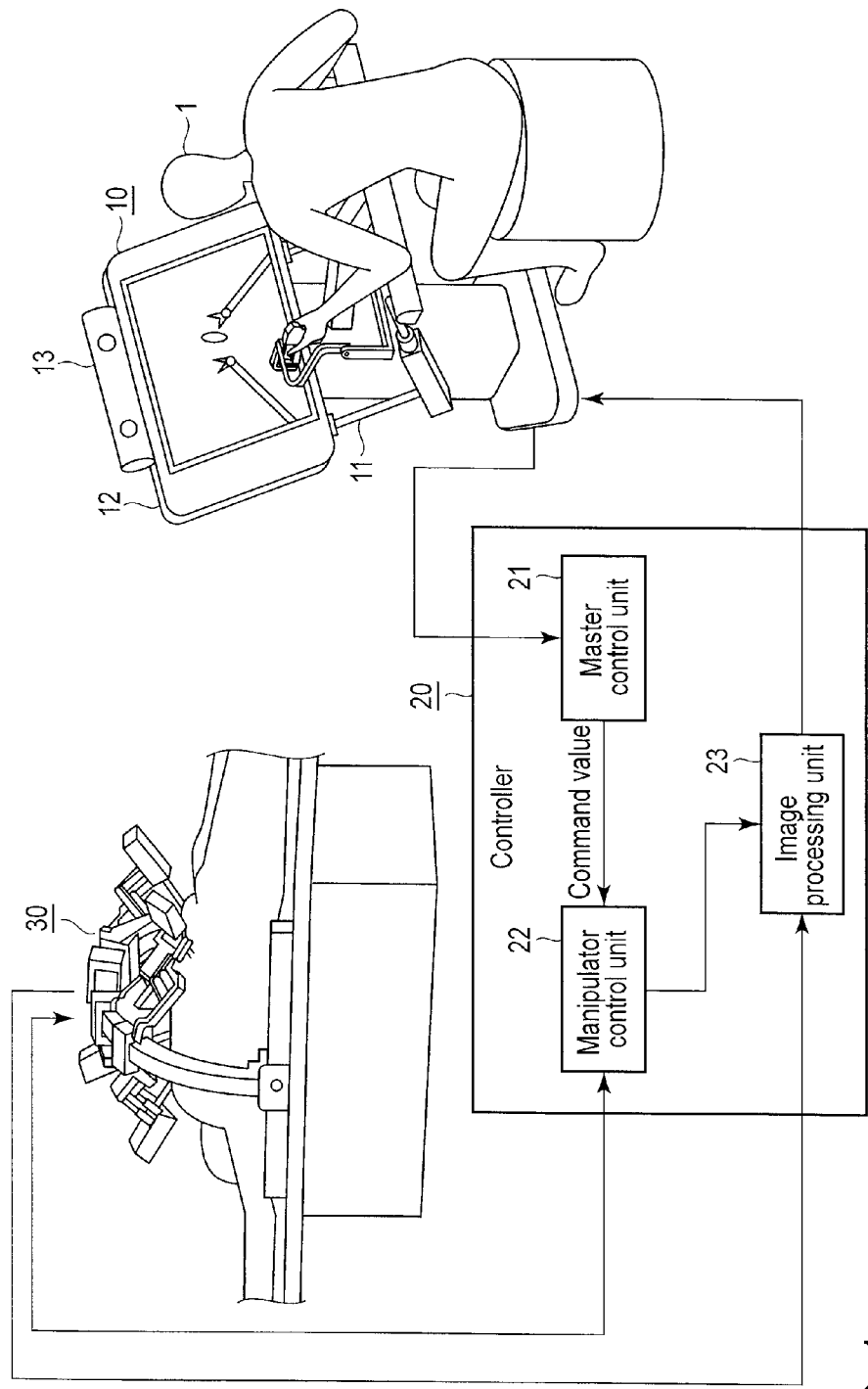
FIG. 1 is a diagram showing an outline of an example of a master-slave manipulator according to a first embodiment of the invention.

A first embodiment of the invention will be described first. FIG. 1 is a diagram showing an outline of an example of a master-slave manipulator according to the first embodiment of the invention. As shown in FIG. 1, the master-slave manipulator comprises a master input device 10, controller 20, and slave manipulator 30.

The master input device 10 comprises an input section 11, display section 12, and image sensor 13 and serves as a master of the master-slave manipulator.

The input section 11 is fixed to, for example, the display section 12 of the master input device 10 and outputs a signal for actuating the slave manipulator 30 when it is operated by an operator 1. The input section 11 will be described in detail later.

The display section 12 comprises, for example, a liquid-crystal display and displays an image based on an image signal (described later) input from the controller 20. The input image signal is obtained by processing, in the controller 20, an image signal captured by an electronic camera (electronic endoscope) attached to the slave manipulator. The operator 1 of the master input device 10 can recognize an image of the distal end of the slave manipulator 30, which is located in a place distant from the input device 10, by displaying an image based on the processed image signal on the display section 12.

The image sensor 13 is, for example, a twin-lens sensor with two spaced lenses. The image sensor 13 optically captures and produces two images of the input section 11 having a predetermined parallax. The image sensor 13 will be described in detail later.

The controller 20 comprises a master control unit 21, manipulator control unit 22, and image processing unit 23.

The master control unit 21, which serves as an example of a first control unit, calculates the position/orientation of the distal end of the input section 11 of the master input device 10 in response to a signal from the input device 10. In order to calculate the position/orientation of the distal end of the input section 11, according to the present embodiment, the master input device 10 comprises detection units (sensors) of two or more systems configured to individually detect different physical quantities, which will be described later. Based on outputs from these sensors of the two or more systems, the master control unit 21 calculates the position/orientation of the distal end of the input section 11. Then, the master control unit 21 outputs the value of the calculated position/orientation as a command value of the position/orientation of the distal end of the slave manipulator to the manipulator control unit 22.

The manipulator control unit 22, which serves as an example of a second control unit, receives the position/orientation command value from the master control unit 21, and calculates necessary drive amounts of joints of the slave manipulator 30 to adjust the position/orientation of the distal end of the slave manipulator to the command value by, for example, an inverse kinematics computation. The manipulator control unit 22 drives the joints of the slave manipulator according to the calculated drive amounts.

The image processing unit 23 processes an image signal captured by the electronic camera (electronic endoscope or the like) attached to the distal end of the slave manipulator, produces a display image signal for the display section 12, and outputs it to the display section 12.

The slave manipulator 30 comprises a plurality of joints corresponding to degrees of freedom. The joints of the slave manipulator 30 are driven according to a control signal from the manipulator control unit 22.

FIG. 2 is a view illustrating duplexing of sensors for detecting the position/orientation of the input section 11 of the master input device according to the present embodiment.

The input section 11 comprises a grip unit 100 for use as an operating unit on its distal end. A plurality of links are connected to the grip unit 100 through the joints, individually. The joints shown in FIG. 2 include rotary joints and translational joints. As the operator 1 holds and operates the grip unit 100, the joints rotate or move linearly in response to the operation. FIG. 2 shows an example in which the input section 11 comprises six joints, including four rotary joints and two translational joints. These six joints can provide six degrees of freedom (three for position plus three for orientation) for the grip unit 100. The link structure of FIG. 2 is given as an example only and may alternatively be configured to comprise different numbers of rotary and translational joints. The number of degrees of freedom for the operating unit is not limited to six. The operating unit shown in FIG. 2 is for right-hand use. A left-handed operating unit can be constructed by only reversing the right and left of the right-handed one. The substantial construction of the left-handed operating unit is the same as the one shown in FIG. 2.

Sensors (e.g., encoders) 200, 202, 204, 206, 208 and 210 for detecting the amounts of rotation or translational motion of the joints are arranged near the joints. Output signals from these encoders are input to the master control unit 21. In FIG. 2, the encoder 200 is a sensor that outputs a signal corresponding to a rotation amount $\theta_1$ of the joint farthest from the grip unit 100. The encoder 202 is a sensor that outputs a signal corresponding to a translational-motion amount $d_1$ of the joint next farthest from the grip unit 100. The encoder 204 is a sensor that outputs a signal corresponding to a translational-motion amount $d_2$ of the joint next farthest from the grip unit 100. Likewise, the encoders 206 and 208 are sensors that output signals corresponding to rotation amounts $\theta_2$ and $\theta_3$ of the joints, respectively. The encoder 210 is a sensor that outputs a signal corresponding to a rotation amount $\theta_4$ of the joint nearest to the grip unit 100.

Further, three reflective markers 450, 452 and 454 are arranged on the grip unit 100. These markers are formed using a highly reflective material such that they can be highlighted in an image captured by the image sensor 13. The markers 450 to 454 should preferably be located on the grip unit 100 in such a manner that they are differently spaced apart from one another. Preferably, moreover, the three markers 450 to 454 should be arranged so that they are not in a straight line and can be recognized by the image sensor 13 even when the orientation of the grip unit 100 or operating unit is changed. This is done in order that the markers 450 to 454 can be correctly identified when they are extracted on the image. The feature points of the operating unit obtained by the image sensor 13 are not limited to the reflective markers. For example, the feature points of the operating unit may alternatively be luminous bodies such as LEDs.

The image sensor 13 comprises twin-lens imaging systems 402 and 404. Each of the imaging systems 402 and 404 comprises an imaging optical system and image-pickup device and is located at a predetermined distance from the input section 11. The imaging systems 402 and 404 are spaced apart from each other at a predetermined distance.

The imaging optical system is an optical system for focusing incident luminous flux on a light receiving surface of the image-pickup device. The image-pickup device is a sensor that converts the luminous flux incident through the imaging optical system into an electrical signal and produces an image for determining the position/orientation of the grip unit 100. The image produced by the image-pickup device is input to the master control unit 21.

Figure 3:
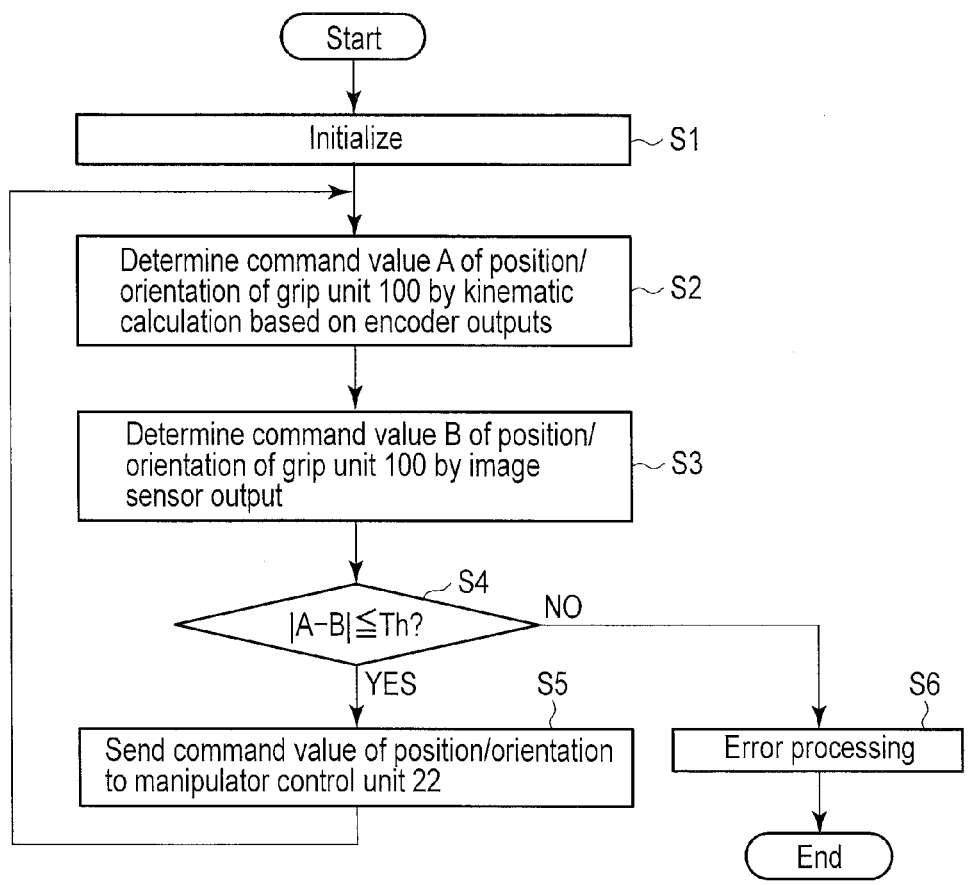
FIG. 3 is a flowchart illustrating the operation of the master-slave manipulator according to the first embodiment.

The following is a description of the operation of the master-slave manipulator according to the first embodiment of the invention. FIG. 3 is a flowchart illustrating the operation of the master-slave manipulator, especially that of the master control unit 21.

The master-slave manipulator is initialized first (Step S1). In this initialization, the operator 1 sets the position/orientation of the grip unit 100 to, for example, a predetermined initial position/orientation. Thereafter, the operator 1 actuates the imaging systems 402 and 404 of the image sensor 13 to acquire an image of the grip unit 100 including the markers 450 to 454. Alternatively, the position/orientation of the grip unit 100 may be automatically set.

The master control unit 21 extracts the markers 450 to 454 as feature points from the image captured by the imaging systems 402 and 404. The markers 450 to 454 in the image can be extracted by, for example, the conventional pattern matching method.

After the markers 450 to 454 in the image are extracted, the master control unit 21 sets a three-dimensional coordinate system (camera coordinate system) C in the captured image. Based on this camera coordinate system C, the control unit 21 calculates an orientation matrix P, which is indicative of the initial position/orientation of the grip unit 100. In the camera coordinate system C, for example, X-, Y-, and Z-axes are used to represent the horizontal, vertical, and depth directions, respectively, of the image, and the coordinate of the marker 454 is set on the origin. Thereupon, the orientation matrix P can be given as a three-by-three matrix comprising unit vectors indicative of the directions of the X-, Y-, and Z-axes or a four-by-four matrix comprising a position vector in addition to these unit vectors.

After calculating the orientation matrix P, the master control unit 21 calculates a transformation matrix Q used to transform the orientation matrix P of the camera coordinate system C into an orientation matrix viewed in a world coordinate system (e.g., a coordinate system based on the ground level) W. When the transformation matrix Q is calculated, the initialization is completed.

If the operator 1 operates the grip unit 100 after the initialization, the position/orientation of the grip unit 100 changes in response to the operation. The output signals from the encoders 200 to 210 change based on the change of the position/orientation. The master control unit 21 performs a kinematic calculation based on amounts of translational motion and rotation indicated by the output signals from the encoders 200 to 210, thereby calculating a command value A of the position/orientation of the grip unit 100 (Step S2).

Further, the master control unit 21 calculates a command value B of the position/orientation of the grip unit 100 based on the image captured by the image sensor 13 (Step S3).

A change in the position (displacement) of the grip unit 100 in the image can be calculated based on that of the marker (e.g., marker 454) in the origin position between images of the grip unit 100 captured by the image sensor 13 before and after the change of the position/orientation. A change in position in the Z-direction can be calculated based on a deviation between positions of the marker 454 in the images captured individually through the imaging systems 402 and 404. The deviation is caused by parallax between the imaging systems 402 and 404. The deviation is calculated by, for example, the image correlation method.

Further, a change in the orientation (amount of rotation) of the grip unit 100 in the image can be calculated based on changes in position of the remaining markers relative to the marker (e.g., marker 454) in the origin position between the images of the grip unit 100 captured by the image sensor 13 before and after the change of the position/orientation.

Although the twin-lens imaging systems are used in the example described above, a single-lens imaging system may be used instead. In this case, depth coordinates can be determined according to the size of the marker image on the image sensor 13. Further, the position/orientation of the operating unit can be determined by using three markers that are not arranged in a straight line. Since this technique is conventional, a detailed description thereof is omitted.

After calculating the command value of the position/orientation of the grip unit 100 viewed through the camera coordinate system C, the master control unit 21 calculates an orientation matrix P' viewed through the camera coordinate system C after the change of the position/orientation by multiplying the orientation matrix P by a matrix indicative of translation represented by the variation of the position of the grip unit 100 and a rotation matrix represented by the amount of rotation of the grip unit 100. Thereafter, the master control unit 21 calculates the command value B of the position/orientation of the grip unit 100 viewed in the world coordinate system by multiplying the orientation matrix P' by the transformation matrix Q.

After calculating the command values A and B of the position/orientation, the master control unit 21 determines whether the absolute value of the difference between the command values A and B is not more than a predetermined value Th (Step S4). The command values A and B both represent the position/orientation of the grip unit 100 after the operation by the operator 1 and are originally substantially equal. Thus, a failure, if any, of any of the encoders 200 to 210 or the image sensor 13 can be determined by determining whether the absolute value of the difference between the command values A and B is not more than the predetermined value Th.

If the absolute value of the difference between the command values A and B is determined to be not more than the predetermined value Th in Step S4, the master control unit 21 outputs the command value A or B (or an average between these values) to the manipulator control unit 22 (Step S5). On receiving this, the manipulator control unit 22 calculates, by an inverse kinematics computation, the necessary drive amounts of the joints to adjust the position/orientation of the distal end portion of the slave manipulator 30 to the command value of the position/orientation input from the master control unit 21. Based on the calculated drive amounts, thereafter, the manipulator control unit 22 drivingly controls the joints of the slave manipulator 30. Thereupon, a series of operations of the master-slave manipulator ends.

If the absolute value of the difference between the command values A and B is determined to be more than the predetermined value Th in Step S4, the master control unit 21 performs error processing (Step S6). The error processing may be, for example, processing to prevent the calculated command value from being delivered to the manipulator control unit 22, processing to warn the operator 1 of a failure of any of the encoders 200 to 210 or the image sensor 13, or processing to shut down the system of the master-slave manipulator. Also in case of this error processing, a series of operations of the master-slave manipulator ends.

According to the present embodiment, as described above, the command value of the position/orientation of the grip unit 100 is calculated based on outputs from sensors of two systems configured to individually detect different physical quantities, including the encoders as first sensors for detecting the displacements and rotation amounts of the joints attached to the input section 11 and the image sensor as a second sensor configured to pick up images. Thus, for example, a failure can be easily detected.

In the flowchart of FIG. 3, moreover, the error processing is performed if there is a difference not less than the predetermined value between the command values A and B. If any of the output signals from the encoders or the image sensor is determined to be faulty by an inspection after the error processing, the slave manipulator 30 can thereafter be drivingly controlled using a faultless signal. Thus, this arrangement is resistant to failure.

As in the prior art technique, two types of sensors (e.g., a combination of an encoder and limit switch or potentiometer) for sensor duplexing may be disposed on the same joint to obtain the same physical quantity. In this case, the two sensors may be simultaneously caused to fail by heat or submergence. In the case that the command value of the position/orientation of the grip unit 100 is calculated based on the image captured by the image sensor, as in the present embodiment, the image sensor need not be disposed on the joints of the input section 11. Thus, the encoder and image sensor can be prevented from simultaneously failing.

In the example described above, the three markers 450 to 454 are arranged on the grip unit 100 of the input section 11, and the image sensor 13 is located apart from the input section 11. As shown in FIG. 4, in contrast, an image sensor 410 may be attached to the grip unit 100 with markers 460, 462 and 464 located apart from the input section 11. Further, the markers may be omitted. In this case, for example, the position/orientation of the operating unit is determined with outline portions of the grip unit 100 used as feature points on the image.

In the example described above, moreover, the markers 450 to 454 are differently spaced apart from one another in order that they can be identified in the image. Alternatively, however, the markers may be varied in, for example, reflectance, diameter, or color. In the case that luminous bodies such as LEDs are used in place of the markers to be recognized by the image sensor, the light emission pattern (light emission interval) of the luminous bodies may be changed. The markers of this active type, compared with passive markers such as the reflective markers, are recognized by various techniques.

Second Embodiment

The following is a description of a second embodiment of the invention. The second embodiment is an example in which a command value of the orientation of a grip unit 100 is determined as a command value B based on the output of a gyro sensor.

FIG. 5 is a view illustrating duplexing of sensors for detecting the position/orientation of an input section 11 of a master input device according to the present embodiment. A repeated description of like portions shown in FIGS. 2 and 5 is omitted. The configuration shown in FIG. 5 differs from that shown in FIG. 2 in that only a single marker 454 is disposed on a grip unit 100 and a gyro sensor 600 is attached to the grip unit 100.

The gyro sensor 600 is a three-axis sensor configured to output a signal corresponding to an angular speed produced in the grip unit 100 around X-, Y-, and Z-axes of a world coordinate system W. An amount of rotation as a variation of the orientation of the grip unit 100 is detected by integrating the angular speed signal.

Figure 6:
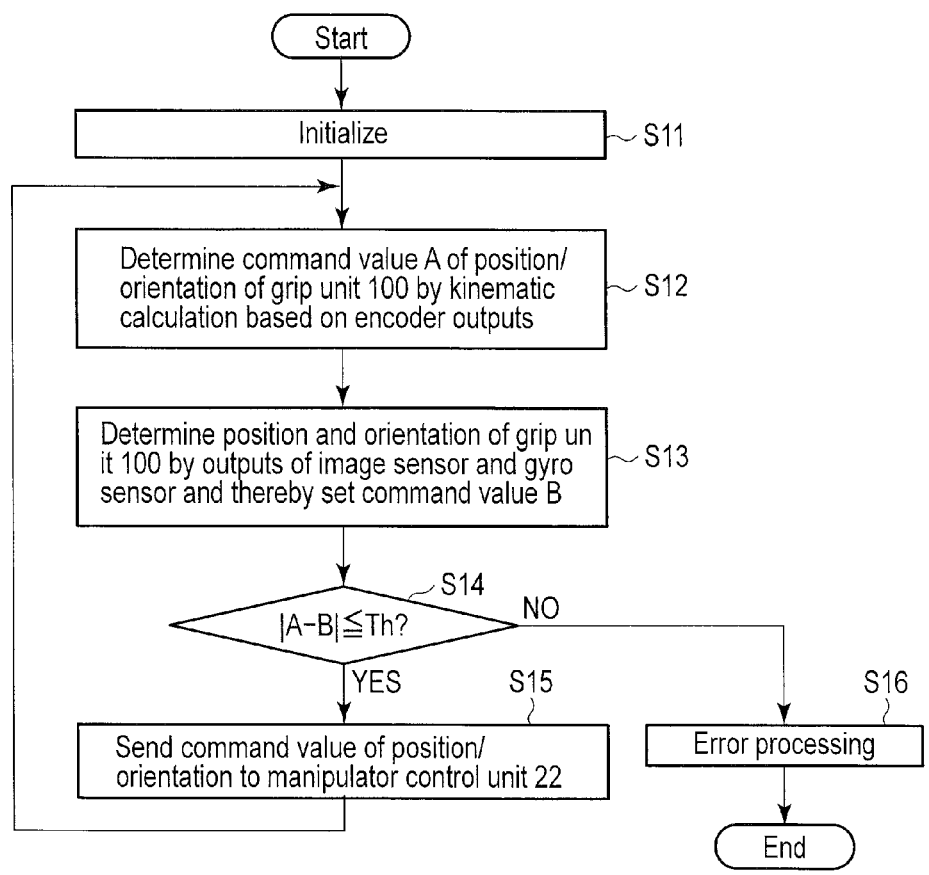
FIG. 6 is a flowchart illustrating the operation of a master-slave manipulator according to the second embodiment.

The following is a description of the operation of a master-slave manipulator according to the second embodiment of the invention. FIG. 6 is a flowchart illustrating the operation of the master-slave manipulator. A repeated description of like portions shown in FIGS. 3 and 6 is omitted.

As in the first embodiment, the master-slave manipulator is initialized first (Step S11). In the initialization of the second embodiment, only a position transformation matrix should only be determined without the necessity of determining an orientation transformation matrix. The position transformation matrix is a transformation matrix that is used to transform a matrix indicative of translation relative to X-, Y-, and Z-axes set in a camera coordinate system C into a matrix indicative of translation viewed in the world coordinate system (e.g., a coordinate system based on the ground level) W.

If the operator 1 operates the grip unit 100 after the initialization, the position/orientation of the grip unit 100 changes in response to the operation. Output signals from encoders 200 to 210 change based on the change of the position/orientation. A master control unit 21 performs a kinematic calculation based on amounts of translational motion and rotation indicated by the output signals from the encoders 200 to 210, thereby calculating a command value A of the position/orientation of the grip unit 100 (Step S12).

Further, the master control unit 21 calculates the position of the grip unit 100 based on an image captured by an image sensor 13, calculates the orientation of the grip unit 100 based on the output signal of the gyro sensor 600, and sets the resulting values as a command value B of the position/orientation (Step S13).

The position of the grip unit 100 can be calculated based on the image in the same manner as in the first embodiment. In the second embodiment, the orientation of the grip unit 100 is not calculated based on the image, so that only one marker is sufficient for the purpose. To avoid interception from the image sensor, however, two or more markers may be used.

Since the processing of Step S14 and subsequent steps is the same as the processing of Step S4 to S6 of FIG. 3, a description thereof is omitted.

According to the present embodiment, as described above, the command value of the position/orientation of the grip unit 100 is calculated based on outputs from sensors of two systems configured to individually detect different physical quantities, including the encoders, as first sensors, configured to detect the displacements and rotation amounts of joints attached to the input section 11, the image and gyro sensors, as second sensors, configured to pick up images and detect the angular speed of the grip unit 100, respectively. Thus, the same effect as the first embodiment can be obtained.

Further, the calculation accuracy of the command value of the orientation of the grip unit 100 can be improved by calculating the command value from the output of the gyro sensor, not from the image.

Figure 7:
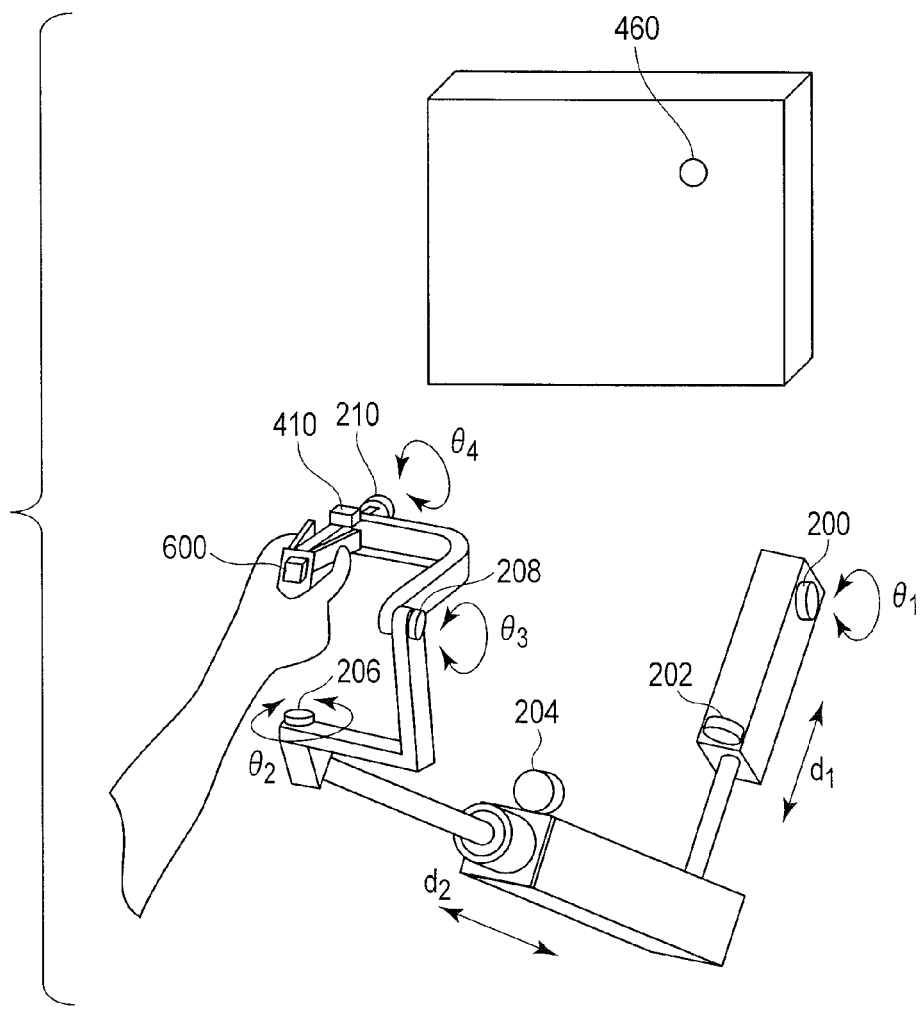
FIG. 7 is a view showing a modification of the second embodiment in which the relative positions of an image sensor and markers are reversed.

In the example described above, the marker 454 is disposed on the grip unit 100 of the input section 11, and the image sensor 13 is located apart from the input section 11. As shown in FIG. 7, in contrast, an image sensor 410 may be attached to the grip unit 100 with a marker 460 located apart from the input section 11. Further, the marker may be omitted. In this case, for example, outline portions of the grip unit 100 are used as feature points on the image.

Third Embodiment

The following is a description of a third embodiment of the invention. The third embodiment is an example in which command values of the position and orientation of a grip unit 100 are determined as a command value B from an acceleration sensor and gyro sensor, respectively.

Figure 8:
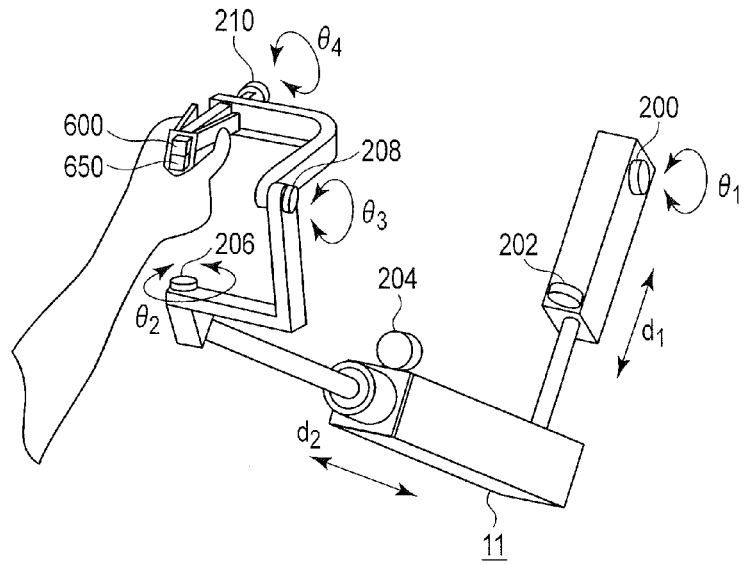
FIG. 8 is a view illustrating duplexing of sensors for detecting the position/orientation of an operating unit of a master input device according to a third embodiment of the invention.

FIG. 8 is a view illustrating duplexing of sensors for detecting the position/orientation of an input section 11 of a master input device according to the present embodiment. A repeated description of like portions shown in FIGS. 5 and 8 is omitted. The configuration shown in FIG. 8 differs from that shown in FIG. 5 in that a gyro sensor 600 and acceleration sensor 650 are arranged on the grip unit 100.

The acceleration sensor 650 is a three-axis sensor configured to output signals corresponding to accelerations individually parallel to X-, Y-, and Z-axes of a world coordinate system W. A displacement as a variation of the position of the grip unit 100 is detected by integrating the acceleration signal twice.

Figure 9:
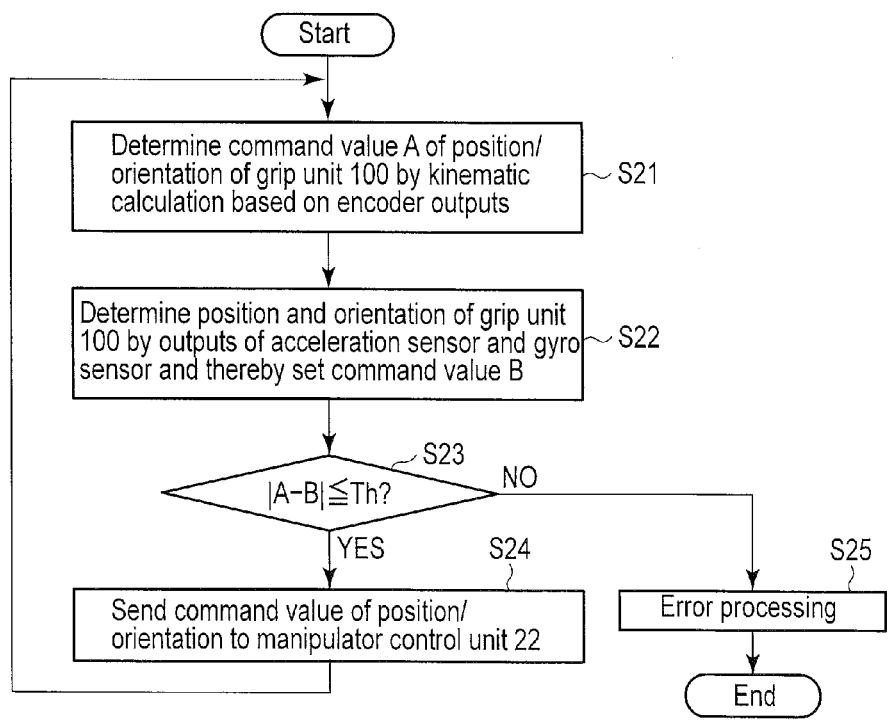
FIG. 9 is a flowchart illustrating the operation of a master-slave manipulator according to the third embodiment.

The following is a description of the operation of a master-slave manipulator according to the third embodiment of the invention. FIG. 9 is a flowchart illustrating the operation of the master-slave manipulator. A repeated description of like portions shown in FIGS. 6 and 9 is omitted.

If the operator 1 operates the grip unit 100, the position/orientation of the grip unit 100 changes in response to the operation. Output signals from encoders 200 to 210 change based on the change of the position/orientation. A master control unit 21 performs a kinematic calculation based on amounts of linear motion and rotation indicated by the output signals from the encoders 200 to 210, thereby calculating a command value A of the position/orientation of the grip unit 100 (Step S21).

Further, the master control unit 21 calculates the command values of the orientation and position of the grip unit 100 based on output signals from the gyro sensor 600 and acceleration sensor 650, respectively. Thereafter, the master control unit 21 sets, as the command value B, the command values of the position and orientation of the grip unit 100 obtained from the acceleration sensor and gyro sensor, respectively (Step S22).

Since the processing of Step S23 and subsequent steps is the same as the processing of Step S4 to S6 of FIG. 3, a description thereof is omitted.

According to the present embodiment, as described above, the command value of the position/orientation of the grip unit 100 is calculated based on outputs from sensors of two systems configured to individually detect different physical quantities, including the encoders, as first sensors, configured to detect the displacements and rotation amounts of joints attached to the input section 11, and the acceleration and gyro sensors, as second sensors, configured to detect the acceleration and angular speed of the grip unit 100, respectively. Thus, the same effect as the first and second embodiments can be obtained.

In calculating the position, the influence of a gravitational acceleration must be removed from the output value of the acceleration sensor. A method for this calculation is disclosed in, for example, Jpn. Pat. Appln. KOKAI Publication No. 2010-273765. In order to discriminate the gravitational acceleration from an acceleration produced by a displacement of an operating unit, a correction may be made using the output of the gyro sensor.

Fourth Embodiment

The following is a description of a fourth embodiment of the invention. The fourth embodiment is an example in which a command value of the position/orientation of a grip unit 100 is determined as a command value B based on the output of an ultrasonic sensor.

Figure 10:
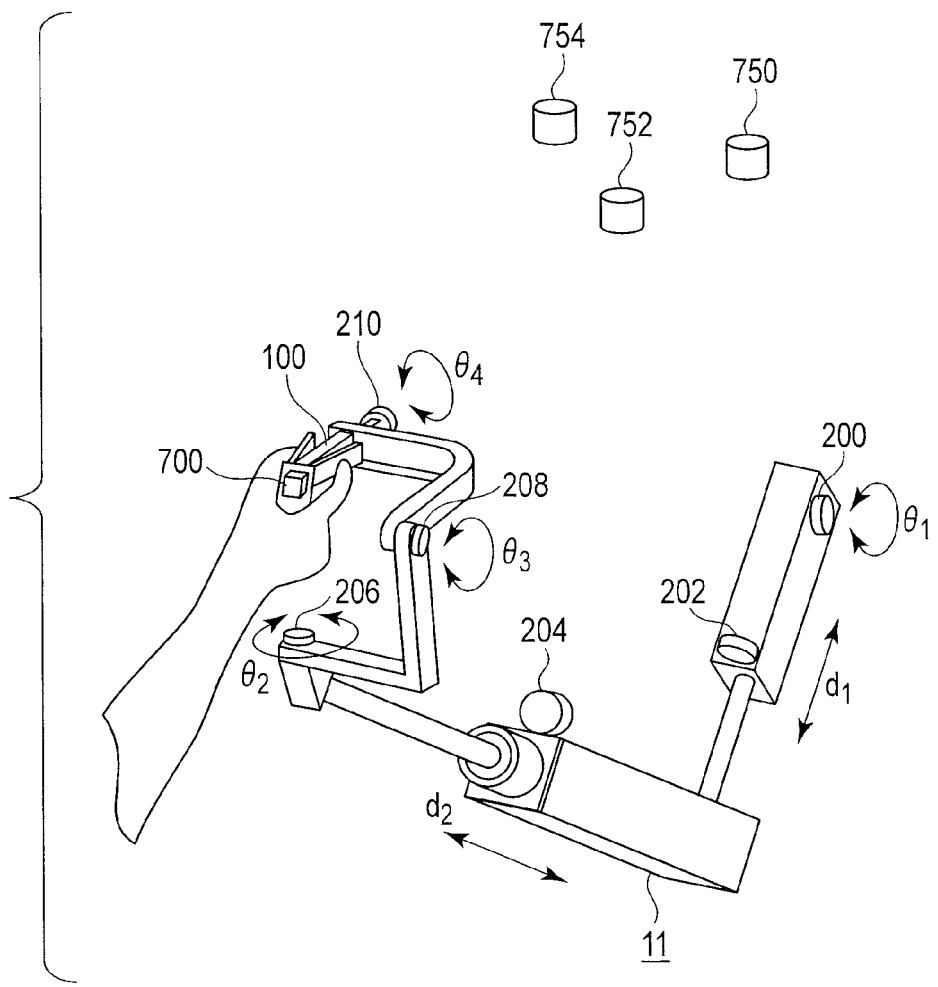
FIG. 10 is a view illustrating duplexing of sensors for detecting the position/orientation of an operating unit of a master input device according to a fourth embodiment of the invention.

FIG. 10 is a view illustrating duplexing of sensors for detecting the position/orientation of an input section 11 of a master input device according to the present embodiment. A repeated description of like portions shown in FIGS. 8 and 10 is omitted. The configuration shown in FIG. 10 differs from that shown in FIG. 8 in that an ultrasonic sensor 700 is disposed on the grip unit 100 and three ultrasonic generators 750, 752 and 754 are located apart from the input section 11.

The ultrasonic sensor 700 detects ultrasonic signals produced by the ultrasonic generators 750 to 754. The ultrasonic generators 750 to 754 produce ultrasonic waves of different frequencies. The distances between the ultrasonic sensor 700 and ultrasonic generators 750 to 754 can be individually calculated by detecting the elapsed times before reception of the ultrasonic signals from the generators 750 to 754 by the sensor 700. The three-dimensional position/orientation of the grip unit 100 can be calculated based on these distances.

Figure 11:
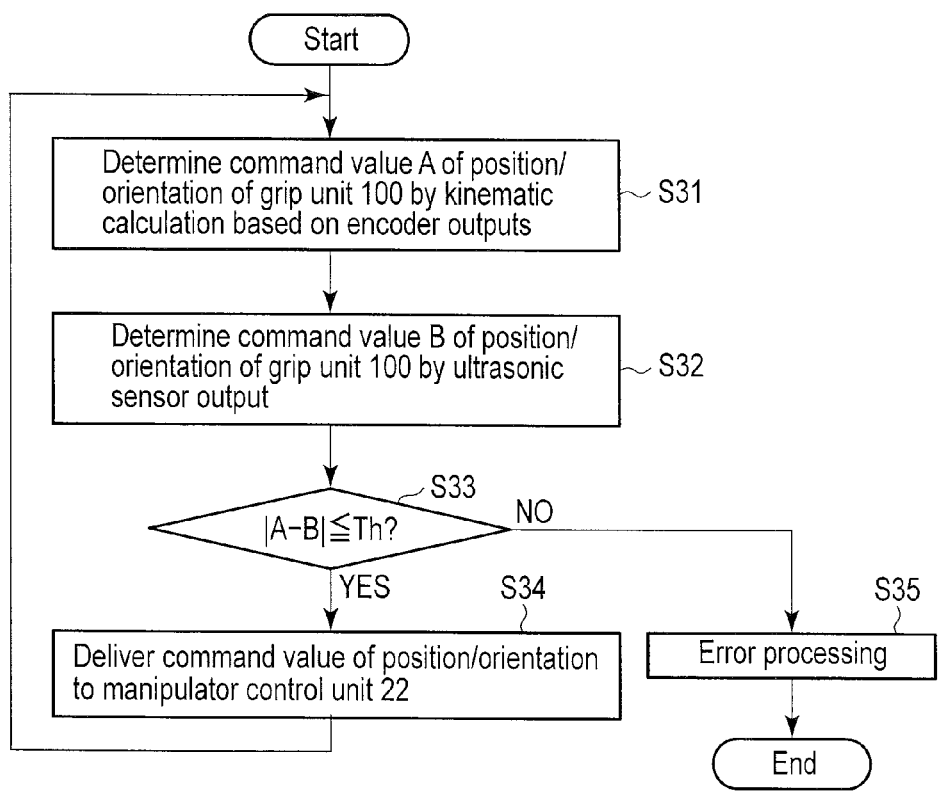
FIG. 11 is a flowchart illustrating the operation of a master-slave manipulator according to the fourth embodiment.

The following is a description of the operation of a master-slave manipulator according to the fourth embodiment of the invention. FIG. 11 is a flowchart illustrating the operation of the master-slave manipulator. A repeated description of like portions shown in FIGS. 9 and 11 is omitted.

If the operator 1 operates the grip unit 100, the position/orientation of the grip unit 100 changes in response to the operation. Output signals from encoders 200 to 210 change based on the change of the position/orientation. A master control unit 21 performs a kinematic calculation based on amounts of linear motion and rotation indicated by the output signals from the encoders 200 to 210, thereby calculating a command value A of the position/orientation of the grip unit 100 (Step S31).

Further, the master control unit 21 calculates the command value B of the position/orientation of the grip unit 100 based on an output signal from the ultrasonic sensor 700 (Step S32).

Since the processing of Step S33 and subsequent steps is the same as the processing of Step S4 to S6 of FIG. 3, a description thereof is omitted.

According to the present embodiment, as described above, the command value of the position/orientation of the grip unit 100 is calculated based on outputs from sensors of two systems configured to individually detect different physical quantities, including the encoders, as first sensors, configured to detect the displacements and rotation amounts of joints attached to the input section 11, and the ultrasonic sensor, as a second sensor, configured to detect the displacement and rotation amount of the grip unit 100. Thus, the same effect as the first to third embodiments can be obtained.

Although the position/orientation of the grip unit 100 is detected by the ultrasonic sensor according to the fourth embodiment, it may alternatively be detected by means of, for example, a magnetic sensor.

While the present invention has been described in terms of the several embodiments, it is to be understood that the invention is not limited to these embodiments but can be modified and applied in various ways without departing from the spirit of the invention. For example, the position/orientation of the grip unit 100 may be detected by means of sensors of three or more systems based on combinations of the sensors described in connection with the first to fourth embodiments.

What is claimed is:
1. A master-slave manipulator comprising:
a master input device for actuating a slave manipulator comprising a plurality of slave-manipulator-side joints, the master input device comprising:
an input section comprising:
a plurality of master-input-device-side joints; and
a grip unit configured to be held and operated by an operator,
wherein the plurality of master-input-device-side joints are configured to be rotated, to be displaced linearly, or both in response to an operation of the grip unit by the operator;

a first detection sensor configured to detect a value of a rotation amount, a displacement amount, or both of the plurality of master-input-device-side joints as a first type of physical quantity representing a position, an orientation, or both of the grip unit; and a second detection sensor configured to detect a value of a second type of physical quantity representing the position, the orientation, or both of the grip unit, wherein the first type of physical quantity is different from the second type of physical quantity; and a controller comprising hardware, the controller being configured to:
calculate:
a first command value based on the value of the first type of physical quantity detected by the first detection sensor, wherein the first command value represents the position, the orientation, or both of the grip unit; and a second command value based on the value of the second type of physical quantity detected by the second detection sensor, wherein the second command value represents the position, the orientation, or both of the grip unit;

determine whether an absolute value of a difference between the first command value and the second command value is not more than a predetermined value; and calculate drive amounts of the plurality of slave-manipulator-side joints based on at least one of the first command value and the second command value when it is determined that the absolute value of the difference between the first command value and the second command value is not more than the predetermined value.

2. The master-slave manipulator according to claim 1, wherein the second detection sensor comprises an image sensor configured to capture an image of the grip unit, wherein a value in the image captured by the image sensor is the value of the second type of physical quantity representing the position, the orientation, or both of the grip unit.

3. The master-slave manipulator according to claim 1, wherein the second detection sensor comprises one of:
an ultrasonic sensor configured to detect an ultrasonic signal, wherein a value of the ultrasonic signal is the value of the second type of physical quantity representing the position, the orientation, or both of the grip unit; and
a magnetic sensor configured to detect a magnetic signal, wherein a value of the magnetic signal is the value of the second type of physical quantity representing the position, the orientation, or both of the grip unit.

4. A master-slave manipulator comprising:
a master input device for actuating a slave manipulator comprising a plurality of slave-manipulator-side joints, the master input device comprising:
an input section comprising:
a plurality of master-input-device-side joints; and
a grip unit configured to be held and operated by an operator,
wherein the plurality of master-input-device-side joints are configured to to be rotated, to be displaced linearly, or both in response to an operation of the grip unit by the operator;
a first detection sensor configured to detect a value of a rotation amount, a displacement amount, or both of the plurality of master-input-device-side joints as a first type of physical quantity representing a position and an orientation of the grip unit; and a second detection sensor configured to detect a value of a second type of physical quantity representing the position and the orientation of the grip unit,
wherein the first type of physical quantity is different from the second type of physical quantity, and
wherein the second detection sensor comprises:
an image sensor configured to capture an image of the grip unit, wherein a value in the image captured by the image sensor is the value of the second type of physical quantity representing the position of the grip unit; and
an angular speed sensor configured to detect an angular speed of the grip unit, the angular speed being the second type of physical quantity representing the orientation of the grip unit; and a controller comprising hardware, the controller being configured to:
calculate:
a first command value based on the value of the first type of physical quantity detected by the first detection sensor, wherein the first command value represents the position and the orientation of the grip unit; and a second command value based on the value of the second type of physical quantity detected by the second detection sensor, wherein the second command value represents the position and the orientation of the grip unit;

determine whether an absolute value of a difference between the first command value and the second command value is not more than a predetermined value; and calculate a drive amount of the slave-manipulator-side joint based on at least one of the first command value and the second command value when it is determined that the absolute value of the difference between the first command value and the second command value is not more than the predetermined value.

5. A master-slave manipulator comprising:
a master input device for actuating a slave manipulator comprising a plurality of slave-manipulator-side joints, the master input device comprising:
an input section comprising:
a plurality of master-input-device-side joints; and
a grip unit configured to be held and operated by an operator,
wherein the plurality of master-input-device-side joints are configured to be rotated, to be displaced linearly, or both in response to the operation of the grip unit by the operator;
a first detection sensor configured to detect a value of a rotation amount, a displacement amount, or both of the plurality of master-input-device-side joints as a first type of physical quantity representing a position and an orientation of the grip unit; and a second detection sensor configured to detect a value of a second type of physical quantity representing the position and the orientation of the grip unit,
wherein the first type of physical quantity is different from the second type of physical quantity, and
wherein the second detection sensor comprises:
an acceleration sensor configured to detect an acceleration of the grip unit, the acceleration being the second type of physical quantity representing the position of the grip unit; and
an angular speed sensor configured to detect an angular speed of the grip unit, the angular speed being the second type of physical quantity representing the orientation of the grip unit; and a controller comprising hardware, the controller being configured to:

calculate:
- a first command value based on the value of the first type of physical quantity detected by the first detection sensor, wherein the first command value represents the position and the orientation of the grip unit; and
- a second command value based on the value of the second type of physical quantity detected by the second detection sensor, wherein the second command value represents the position and the orientation of the grip unit;

determine whether an absolute value of a difference between the first command value and the second command value is not more than a predetermined value; and calculate a drive amount of the plurality of slave-manipulator-side joints based on at least one of the first command value and the second command value when it is determined that the absolute value of the difference between the first command value and the second command value is not more than the predetermined value.

* * * * *